United States Patent [19]

Engler et al.

[11] Patent Number: 5,262,316
[45] Date of Patent: Nov. 16, 1993

[54] GENETICALLY TRANSFORMED PEPPER PLANTS AND METHODS FOR THEIR PRODUCTION

[75] Inventors: Dean E. Engler, El Cerrito, Calif.; Assaf Z. Guri, Cherry Hill; James A. Lauritis, Maple Shade, both of N.J.; Lucille M. P. Schloemer, El Cerrito, Calif.

[73] Assignee: DNA Plant Technology Corporation, Oakland, Calif.

[21] Appl. No.: 796,152

[22] Filed: Nov. 22, 1991

[51] Int. Cl.$^5$ .................. C12N 15/00; C12N 5/00
[52] U.S. Cl. ...................... 435/172.3; 435/240.45; 435/240.54
[58] Field of Search .................. 800/205; 435/172.3, 435/240.45, 240.48, 240.49, 240.5, 240.51, 240.54

[56] References Cited

FOREIGN PATENT DOCUMENTS 0249432 9/1987 European Pat. Off. .

OTHER PUBLICATIONS

Saito et al. (1989) Annual Mtg. of Am. Soc. of Plant Physiol. Abstr. 77.
Liu et al. (1990) Plant Cell Rep. 9:360-364.
Gunay et al. (1978) Plant Science Letters 11:365-372.
Agrawal et al. (1983) Current Science 52:645-646.
Phillips et al. (1985) Plant Cell, Tissue and Organ Culture 4:261-269.
Lee et al. (1988) Hort. Science 23:130, Abstr. 482.
Agrawal et al. (1989) Plant Cell, Tissue and Organ Culture 16:47-55.
Shao et al. (1989) Amer. J. Botany 76:185;14 86, Abstr. 491.
Ochoa-Alejo et al. (1990) Scientia Hort. 42:21-28.
Arroyo et al. (1991) Plant Cell Rep. 10:414-416.
Jacobs et al. (1990) Hort. Science 25:120, Abstr. 408.
Saxena et al. (1981) Protoplasma 108:357-360.
Diaz et al. (1988) Plant Cell Rep. 7:210-212.
Hilliard et al. (1989) Annual Mtg. of Tissue Culture Assoc. Abstr. 70.
Weier et al., "Botany", published 1982 by John Wiley and Sons (New York, N.Y.), p. 343.
Hinchee, M., et al. Bio/Technology, vol. 6, (1988) pp. 915-922.
Puonti-Kaerlas, J., et al. Plant Cell Reports, vol. 8, (1989) pp. 321-324.
Boulton, M., et al. Plant Molecular Biology, vol. 12 (1989) pp. 31-40.
Bolton, G., et al. Science, vol. 232 (1986) pp. 983-985.
Lee, K., et al. The EMBO Journal, vol. 7, (1988) pp. 1241-1248.
Chi, G. K., et al. Plant Science, vol. 64 (1989) 243-250.
Wickremesinhe, E., et al. Hort Science, vol. 25 (1990) pp. 1436-1439.
Davies, P. J., "The Plant Hormones: Nature, Occurrence, Functions", in: *Plant Hormones and Their Role in Plant Growth and Development*, Dordrecht, Martinus, Nijhoff, 1987) pp. 1-11.

*Primary Examiner*—David T. Fox
*Assistant Examiner*—Charles Rories
*Attorney, Agent, or Firm*—Townsend and Townsend Khourie and Crew

[57] ABSTRACT

Pepper explant material is transformed by incubation with Agrobacterium cells carrying an exogenous DNA sequence. The pepper explant is preferably obtained from either the young embryonic cotyledon or the young expanded cotyledon, and transformed shoots are preferably induced directly in the explant material without passage through a callus phase. Whole transformed pepper plants may be regenerated from the transformed shoots by rooting and subsequent planting in the soil. The exogenous DNA will be stably incorporated into the chromosomes of the regenerated pepper plant which will be able to express gene(s) encoded by the DNA sequence. An improved method for regenerating pepper plants, without transformation, is also described. Regeneration to produce tetraploids is a further embodiment of this invention.

37 Claims, 1 Drawing Sheet

FIG. IA.
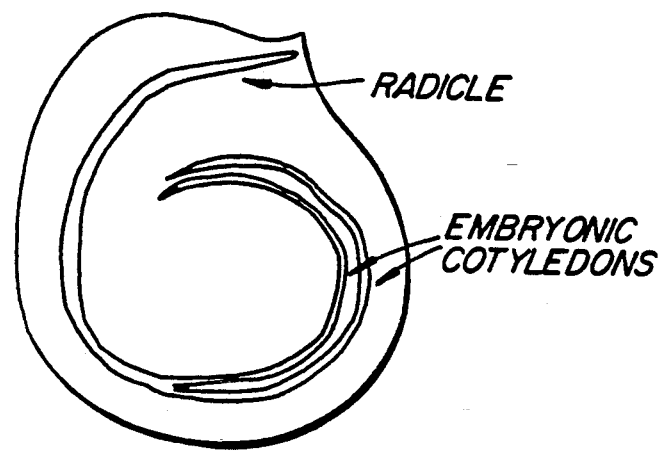
FIG. IB.
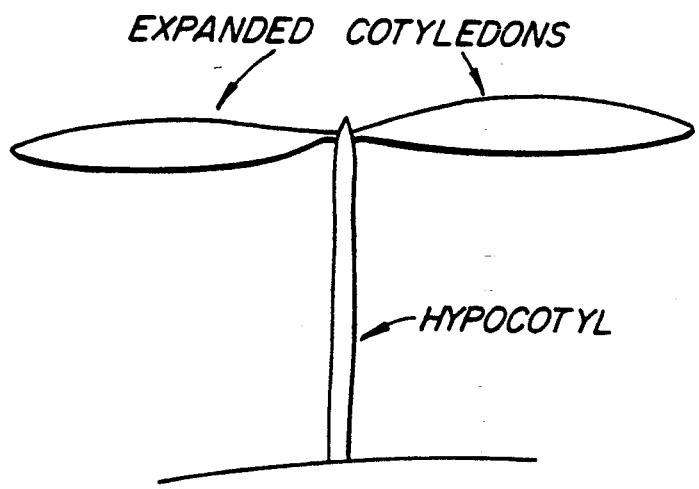
FIG. 2.

GENETICALLY TRANSFORMED PEPPER PLANTS AND METHODS FOR THEIR PRODUCTION

BACKGROUND OF THE INVENTION

Field of the Invention

The present invention relates generally to methods for genetically altering higher plant materials and reproducing whole plants therefrom. More particularly, the invention relates to a method for genetically transforming and regenerating pepper plants. The result of transformation coupled with regeneration is a pepper line or plant containing introduced DNA capable of expression. The invention further comprises an improved method of regenerating pepper (without transformation). Regeneration without transformation can be used for propagation or to produce variants of pepper, e.g., somaclonal variants, with a new characteristic. The new characteristic may be polyploidy (e.g., a tetraploid pepper).

Pepper is of the genus *Capsicum,* which is of the family Solanaceae, subfamily Solanoideae and tribe Solaneae. This genus includes the species *Capsicum annuum* and *Capsicum frutescens.* Peppers are cultivated and used around the world as sweet peppers such as the bell pepper; or as pungent chili peppers, jalapeno peppers, and Tabasco peppers (used to make Tabasco sauce); or as a source of dried powders of various colors such as paprika.

The types of cultivated peppers can be differentiated by pungency, fruit shape, and size. Non-pungent peppers used for the fresh market include the large, blocky, thick-fleshed Bell or Stuffing type (e.g., cv.s (cultivars) California Wonder, Yolo Wonder, Keystone Giant and Dulce Italians) and the medium-sized, heart-shaped, thick-fleshed Pimiento type (e.g., cv.s Pimiento, Pimiento Select, Pimiento Perfection, and Super Red Pimiento) peppers, and the long, blunt-ended, thin fleshed Cuban type (e.g., cv.s Cubanelle, and Aconcagua). Mildly pungent peppers used for the fresh market and for processing include the long, heart-shaped, thin-fleshed Ancho type (e.g., cv.s Mexican Chili, Ancho, and Mulato), and the long, blunt-ended, thin-fleshed Tuscan type (e.g., cv. Pepperoncini) peppers. The slightly more pungent Anaheim Chili (e.g., cv.s Anaheim Chili, Sandia, California Chili, Mild California, and New Mexican Chili) which is used mainly for processing has an elongate fruit which tapers to a point and medium flesh thickness. Pungent peppers used in both the fresh market and for processing include the long, cylindrical-thick fleshed Jalapeno (e.g., cv.s Jalapeno and Mild Jalapeno), the small, slender, tapering Serrano (e.g., cv. Serrano), and the irregularly shaped, thin-fleshed Cayenne (e.g., cv.s Cayenne Long Thick, Cayenne Long Slim, and Cayenne Long Red) peppers. In addition to the above *C. annuum* types, there are various *C. frutescens* type peppers (e.g., cv. Tabasco).

A type of pepper has been developed which does not fit into the above categorizations. It is a pepper with no pungency, but with a long, cylindrical (Jalapeno type) shape. Pepper lines of this type are called VEGIS-WEET (registered trademark), e.g., Vegisweet line 89288-2 and Vegisweet line 89300-1. These pepper lines were developed by conventional breeding using a jalapeno derivative and the low seed gametoclonal variant Bellsweet to develop inbred varieties that exhibited small narrow fruit that were sweet and contained few seeds. See Plant Variety Protection Certificates for Bell-Sweet (PVP 8700124) and for Vegi-Sweet (PVP 8800202); see also U.S. Pat. No. 5,066,830.

As with any valuable plant species, breeders have long used conventional cross-breeding techniques to improve existing varieties and create new cultivars. While improvements have been achieved, cross-breeding techniques are laborious and slow because of the time required to breed and grow successive plant generations.

Conventional breeding methods can only utilize those genes that are present in species that are sexually compatible with Capsicum. Thus, it would be desirable to utilize recombinant DNA technology to produce new pepper varieties and cultivars in a controlled and predictable manner that contain genes both from sexually compatible crops, and from other unrelated plants, animals, bacteria and viruses.

The recombinant DNA manipulation of pepper, however, has been hindered by difficulty in regenerating whole plants from tissue culture, by difficulty in obtaining transformed pepper tissue and ultimately, in linking regeneration with transformation.

For these reasons, it would be desirable to provide improved methods for the recombinant DNA transformation of pepper plant material and the regeneration of whole plants from the transformed material. It would be particularly desirable to be able to introduce desired characteristic(s) to such material(s) and to be able to regenerate viable pepper plantlets from the modified materials. Such methods should be capable of introducing a preselected exogenous gene(s) into the pepper plant material and should permit the selection of transformed shoots which are regenerated from the material. The method should produce regenerated pepper plants which have stably incorporated the gene(s).

Regeneration of pepper plants in the absence of transformation is a method which has several important uses. The method can be used to generate many copies of the regenerated plant (micropropagation). It can also be used to produce valuable sources of variation (e.g., somaclonal variation) which can be used in breeding strategies for pepper improvement. Somaclonal variation can be in the form of single or multiple gene changes (mutations) or in the form of polyploidization (e.g., tetraploids or aneuploids). Tetraploids often have use in breeding strategies because they may exhibit improvements in agronomically important characteristics (e.g., disease resistance and fruit size); they can be used in strategies to induce seedlessness (e.g., via crossing with diploids to produce triploids); or they can be used to facilitate gene transfer from wild relatives via conventional breeding (e.g., to improve chromosome pairing in interspecific hybrids).

Thus, it would be desirable to provide for an improved method for the regeneration of pepper plants in the absence of transformation, and particularly for a method for the regeneration of tetraploid peppers.

Description of the Background Art

Saito et al. (1989) Annual Meeting of American Society of Plant Physiologists, Abstract No. 77 describes the induction of transformed shooty teratomas in *Capsicum annuum* using Agrobacterium to yield callus. Liu et al. (1990) Plant Cell Rep. 9:360-364, describes the Agrobacterium-mediated transformation and attempted regeneration of hypocotyl, cotyledon and leaf explants of *Capsicum annuum*. European Patent 249432 discloses pepper in a list of plants that might be transformed using cotyledon explants.

The regeneration of pepper plants from hypocotyl or cotyledon explants, without transformation, is described in Gunay et al. (1978) Plant Science Letters 11:365-372; Agrawal et al. (1983) Current Science 52:645-646; Phillips et al. (1985) Plant Cell, Tissue and Organ Culture 4:261-269; Lee et al. (1988) Hort. Science 23:130 Abstract 482; Agrawal et al. (1989) Plant Cell, Tissue and Organ Culture 16:47-55; Shao et al. (1989) Amer. J. of Botany 76:185-86 Abstract No. 491; Ochoa-Alejo et al. (1990) Scientia Horticulturae 42:21-28; and Arroyo et al. (1991) Plant Cell Rep. 10:414-416.

The regeneration of pepper plants from leaf explants, without transformation, is described in Jacobs et al. (1990) Hort. Science 25:120 Abstract No. 408.

The regeneration of pepper plants from protoplasts, without transformation, is described in Saxena et al. (1981) Protoplasma 108:357-360 and Diaz et al. (1988) Plant Cell Rep. 7:210-212. The regeneration of pepper plants from callus, without transformation, is described in Hilliard et al. (1989) Annual Meeting of Tissue Culture Association, Abstract No. 70.

SUMMARY OF THE INVENTION

The present invention comprises methods for the genetic transformation of pepper plant material and for producing and selecting viable shoots from the material which express an exogenous DNA sequence which has been introduced. Whole pepper plants expressing the exogenous DNA sequence may be produced by rooting the shoot and subsequently planting the rooted shoot in soil. The pepper plant material is transformed by incubation with Agrobacterium cells carrying the exogenous DNA sequence which typically includes a selectable plant marker gene as well as one or more genes to be expressed. Shoots are regenerated from the pepper plant material and selected, typically by growth on a selection/induction medium which inhibits growth in the absence of the marker. The invention further comprises an improved method of regenerating pepper (without transformation).

In a first preferred aspect of the present invention, the transformed regenerated shoot is obtained from non-callus plant material. That is, the pepper plant material is transformed and regenerated under conditions which produce transformed shoots which do not pass through a callus stage of development. The avoidance of the callus stage is advantageous because it decreases the time needed to obtain a transformed plant. Moreover, it increases the efficiency of transformation, and it reduces the risk of undesired somaclonal variation due to mutations accumulating in the callus due to extended culture times.

In a second preferred aspect of the present invention, the pepper plant material is derived from cotyledons, preferably young expanded cotyledons or young embryonic cotyledons.

Another preferred aspect of the present invention is the use of a plant selectable marker selected from the group consisting of the aadA gene which encodes spectinomycin resistance, the SPT gene which encodes streptomycin resistance, the NPTII gene which encodes kanamycin resistance, the HPT gene which encodes hygromycin resistance, and the ALS gene which encodes chlorsulfuron resistance.

A further preferred aspect of the present invention is the use of high concentrations of 6-benzyladenine (BA) with expanded cotyledons and moderate concentrations of BA with embryonic cotyledons to induce shoot formation.

Additional preferred aspects of the present invention include the use of a sulfonylurea herbicide to select for transformed shoots; the use of gibberellin, in particular $GA_3$, in the elongation or elongation/selection medium, particularly at high concentrations; and the use of an inhibitor of ethylene action, preferably the $Ag^+$ ion, in the elongation or elongation/selection medium.

The present invention further comprises transformed shoots and whole plant materials produced by the above pepper transformation methods. Regeneration to produce tetraploids is a further embodiment of the invention.

The methods of the present invention provide a particularly convenient technique for selectably breeding new pepper cultivars in a predictable and expeditious manner. It is expected that a variety of traits, such as morphology, herbicide resistance, pesticide resistance, disease resistance, environmental tolerance (e.g., temperature, drought, salinity), growth characteristics, nutritional content, taste, and the like, may be intentionally introduced into the regenerated shoots and stably incorporated into the chromosomes of the regenerated whole plants. The methods of the present invention will be suitable for all or most types of peppers.

BRIEF DESCRIPTION OF THE DRAWINGS

FIGS. 1A and 1B are a side view and an end view, respectively of a pepper seed with the coat and top cotyledon removed where the radicle and a preferred source of explant material, the embryonic cotyledon, are identified.

FIG. 2 is a view of the pepper plant seedling where the hypocotyl and a preferred source of explant material, the expanded cotyledons, are identified.

DESCRIPTION OF THE SPECIFIC EMBODIMENTS

According to the present invention, genetically transformed pepper plants are obtained by the selective introduction of exogenous DNA sequence(s) into the chromosomes of cultured pepper plant material. The methods require certain starting materials, including pepper explant material, the DNA sequence(s) to be introduced, Agrobacterium cells to carry the DNA sequence(s) and mediate their transfer to the pepper explant material, and culture media suitable for the steps of cocultivation of pepper explant material and Agrobacterium cells, shoot induction from transformed explant material, shoot selection, shoot elongation, and rooting of selected shoots. Each of the necessary starting materials will be described below in connection with the method of the present invention.

The methods of the present invention are also suitable for regenerating pepper plants from explant material without transformation. Such methods generally comprise the steps of shoot induction of the explant material, shoot elongation, and rooting of viable shoots. The starting materials will generally be the same as those used for corresponding steps in the transformation method described below.

Pepper explant material suitable for use in the present invention may be obtained from virtually any variety or cultivar of the pepper genus, capsicum.

Pepper cotyledon explants are preferred as the starting material for transformation/regeneration (i.e. for cocultivation with Agrobacterium sp.) or for regeneration. See FIGS. 1A and 1B. other explant types may also be used such as other seedling or embryo parts (e.g., radicles or hypocotyls), or mature plant parts such as leaves, roots, stems, petioles and floral parts, or any other explant from which it is possible to induce whole plants to regenerate.

The preferred cotyledon explants are physiologically "young" to enhance occurrence of regeneration. Since temperature is correlated to growth rate (age), any combination of temperature and age of cotyledons resulting in a young physiological age is sufficient. A "young" cotyledon explant in this context is one from which the potential for shoot bud formation has not yet been lost due to excess age. Germination is a useful frame of reference. A germinated seed is one in which the radicle (i.e. embryonic root) has emerged >2 mm. If seeds are germinated at 28° C., they will be suitable for use as a explant source ("young") for up to 12 days after germination. It is preferable to use seedlings germinated at 28° C. as a source of cotyledon explants within 6 days of germination and most preferable to use them within 3 days of germination. If seeds are germinated at cooler temperatures, they can be considered "young" for a longer period of time (e.g., if germinated at 24° C., they should be used within 18 days of germination, preferably within 9 days, and most preferably within 5 days). If seeds are germinated at warmer temperatures, they should be considered "young" for a shorter period of time (e.g., if germinated at 30° C., they should be used within 8 days of germination, preferably within 4 days, and most preferably within 2 days).

The seeds to be used as a source of cotyledon explant tissue may be mature or immature (preferably mature). "Mature" means seeds that have developed within ripened fruit on the plant to full size, that have dried, and are capable of germinating independently. "Immature" means seeds that have developed on the plant to less than full size (insufficient embryo and endosperm development), and are not capable of germinating without supplements. If mature seeds are used, they should be imbibed/germinated at 20°-30° C. (preferably 24°-30° C., most preferably 28° C.). The cotyledons may be used before they have emerged from the seed coat (embryonic cotyledons; FIGS. 1A and 1B) or after they have emerged from the seed coat (expanded cotyledons; FIG. 2), but they should be used while they are still young (as previously defined). If embryonic cotyledons are to be used as an explant source, the seeds should be imbibed using the conditions described above, but they should be used after 1 to 3 days of imbibition. These seeds may be stored in a refrigerator after the imbibition period and may subsequently be used for explant preparation at any time up to 1 year from the initiation of imbibition (preferably up to 3 months). Seeds do not germinate during storage in a refrigerator.

The exogenous DNA sequences to be introduced may be obtained from virtually any source, including bacterial, algal, fungal, foreign plant, endogenous pepper plant, and animal, and will usually include at least one selectable plant marker gene to permit screening and selection of transformed cells (i.e., those cells which have incorporated the exogenous DNA into their chromosomes), as well as one or more "functional" genes which are chosen to provide, enhance, suppress, or otherwise modify expression of a desired trait or phenotype in the resulting plant. Such traits include herbicide resistance, pesticide resistance, disease resistance, environmental tolerance (e.g., temperature, drought, salinity), morphology, growth characteristics, nutritional content, taste, yield, horticultural characteristics, consumer values, and the like.

The functional gene to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenous gene within the plant. It will be appreciated that control of gene expression can have a direct impact on the observable plant characteristics. Other functional "genes" include sense and anti-sense DNA sequences which may be prepared to suppress or otherwise modify the expression of endogenous genes. The use of anti-sense is described generally in van der Krol et al., (1990) Mol. Gen. Genet. 220:204-212, the disclosure of which is incorporated herein by reference. The use of sense DNA sequence(s) is described in various references, including Napoli et al. (1990) Plant Cell, 2:279-289 and van der Krol et al. (1990) Plant Cell, 2:291-299, the disclosures of which are incorporated herein by reference.

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., *Molecular Cloning—A Laboratory Manual*, Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, as well as the database maintained by the United States Patent office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype. Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot (1987) Genetics, 117:771-776; Dooner et al. (1985) Mol. Gen. Genetics, 200:240-246; and Federoff et al. (1984) Proc. Natl. Acad. Sci. U.S.A., 81:3825-3829, the disclosures of which are incorporated herein by reference.

The selectable plant marker gene on the DNA sequences to be inserted will usually encode a function which permits the survival and emergence of transformed shoots in a selective selection/induction medium. Usually, the selectable marker gene will encode antibiotic resistance, with suitable genes including genes coding for resistance to the antibiotic spectinomycin (e.g., the aadA gene), the streptomycin phosphotransferase (SPT) gene coding for streptomycin resistance, the neomycin phosphotransferase (NPTII) gene encoding kanamycin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the the S4 and/or Hra mutations), or other such genes known in the art. Selection based on resistance to sulfonylurea-type herbicides is preferred. Suitable media for selecting pepper shoot material expressing these genes are described hereinbelow.

In addition to the "functional" gene and the selectable marker gene, the DNA sequences may also contain a reporter gene which facilitates screening of the transformed shoots and plant material for the presence and expression of the exogenous DNA sequences. Exemplary reporter genes include β-glucuronidase and luciferase. The use of β-glucuronidase is described in more detail hereinafter.

The exogenous DNA sequences will be introduced to the pepper explant material by incubation with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or inactivate the tumor-causing genes so that they are suitable for use as vector for the transfer of the gene constructs of the present invention. Other plasmids may be utilized in conjunction with Agrobacterium for transferring the DNA sequences of the present invention.

The construction of recombinant Ti plasmids may be accomplished using conventional recombinant DNA techniques, such as those described in Maniatis et al., supra. Frequently, the plasmids will include additional selective marker genes which permit manipulation and construction of the plasmid in suitable hosts, typically bacterial hosts other than Agrobacterium, such as E. coli. Suitable selective marker genes include tetracycline resistance, kanamycin resistance, ampicillin resistance, gentamycin resistance and the like.

The genes within the T-DNA sequences will typically be linked to appropriate transcriptional and translational control sequences which are suitable for the pepper plant host. For example, the gene will typically be situated at a distance from a promoter corresponding to the distance at which the promoter is normally effective in order to ensure transcriptional activity. Usually, a polyadenylation site and transcription termination sites will be provided at the 3'-end of the gene coding sequence. Frequently, the necessary control functions can be obtained together with the structural gene when it is isolated from a target plant of other host. Such intact genes will usually include coding sequences, intron(s), a promoter, enhancers, and all other regulatory elements either upstream (5') or downstream (3') of the coding sequences.

Optionally, a binary vector system may be used to introduce the DNA sequences according to the present invention. A first plasmid vector strain would carry the T-DNA sequence while a second plasmid vector would carry a virulence (vir) region. By incubating Agrobacterium cells carrying both plasmids with the pepper plant material, transfer DNA sequences to the pepper explant material can be achieved. See, Hoekema et al. (1983) Nature 303:179-180, the disclosure of which is incorporated herein by reference.

Any one of a number of T-DNA plasmids can be used with such a binary vector system, although one should be able to select for the binary plasmid. The T-DNA plasmid in a preferred embodiment comprises a heterologous promoter which promotes the transcription of a gene(s) within the exogenous DNA fragment(s). Examples include the Cauliflower Mosaic Virus 35S promoter (Odell et al. (1985) Nature, 313:810-812); or 1' promoter and 2' promoter (Velten et al. (1984) EMBO J. 12:2723-2730) or nopaline synthatase (nos) promoter (Depicker et al. (1982) J. Mol. Appl. Genet. 1:561-573).

Suitable Agrobacterium strains include *Agrobacterium tumefaciens* and *Agrobacterium rhizogenes*. While the wild-type *Agrobacterium rhizogenes* may be used, the *Agrobacterium tumefaciens* is preferably "disarmed," i.e., have its tumor-inducing activity removed, prior to use. Preferred *Agrobacterium tumefaciens* strains include LBA4404, as described by Hoekema et al. (1983) Nature, 303:179-180, and EHA101 as described by Hood et al. (1986) J. Bacteriol., 168:1291-1301. A preferred *Agrobacterium rhizogenes* strain is 15834, as described by Birot et al. (1987) Plant Physiol. Biochem., 25:323-325.

After the Agrobacterium strain(s) carrying the desired exogenous DNA sequence(s) have been prepared, they will usually be cultured for a period of time prior to incubation with the pepper explant material. Initially, the Agrobacterium may be cultured on a solid media including nutrients, an energy source, and a gelling agent. Suitable nutrients include salts, tryptone, and yeast extracts, while most sugars are suitable as the energy source, and the gelling agent can be TC agar (0.6-1.5%), bactoagar (1-2%), Gel-rite ® (0.15-0.5%), or the like. Suitable media include Minimal A, M9, and L-Broth (LB). A preferred medium is Minimal A as described in detail in the Experimental section hereinafter. Usually, the medium will include an antibiotic to select for Agrobacterium carrying the plasmid DNA sequences, e.g., tetracycline at 1-5 mg/l if the marker is tetracycline resistance.

The Agrobacterium cells are typically cultured for about two to five days, preferably in the dark at about 20° C. to 30° C., and are collected while still a white-creamish color, i.e., before browning, typically by being scraped off the solid medium. The cells are scraped off the medium and suspended in a liquid medium, e.g., Minimal A Medium. The pH should be 6.9-7.1, preferably about 7.0. The bacteria are cultured in liquid medium for 8-36 hours (preferably 12-20 hours) on a shaker (50-200 rpm, preferably 100-120 rpm) at 20°-30° C. (preferably 22°-28° C., most preferably 28° C.). At the end of this period the bacteria are diluted to an Optical Density (OD) of 0.3 (see Maniatis) and cultured for 2-6 hours (preferably 4 hours), on a shaker (50-200 rpm, preferably 100-120 rpm) at 20°-30° C. (preferably 22°-28° C., most preferably 28° C.).

The pepper explant material and the Agrobacterium cells carrying the desired exogenous DNA sequence(s) are cocultivated in a suitable cocultivation medium to allow transfer of the DNA sequence(s) to plant cells within the explant material. Shoots are then regenerated directly from the transformed plant cells (i.e., the transformed cells do not pass through an intermediate callus stage) in a suitable selection/induction medium and a suitable elongation/selection medium. The regenerated, transformed shoots may then be rooted in a suitable rooting medium prior to planting of the resulting whole plantlet in soil. Each of these steps and the media suitable for performing such steps will be described in more detail hereinafter.

The cocultivation medium, the induction or selection/induction medium, the elongation or elongation/selection medium, and the rooting medium, are derived from a general pepper medium which comprises nutrients, an energy source, and growth regulators. See in general regarding plant tissue culture methods and media, Plant, Cell, Tissue and Organ Culture, J. Reinert and Y. P. S. Bajaj (eds.) Springer-Verlag, New York. See in general regarding pepper tissue culture methods and media, R. A. Morrison, et.al. "Pepper" in Handbook of Plant Cell Culture Vol 4, Chapter 19 Evans, D. A., Sharp, W. R., and Ammirato, P. V. (Eds.), Macmillan (1986), and M. Fari, "Pepper (*Capsicum annuum L.*)" in Biotechnology in Agriculture and Forestry Vol. 2: Crops I Bajaj, Y. P. S. (ed.) Springer-Verlag (1986).

The nutrients should be in the form of conventional macronutrient and micronutrient salts, including nitrogen and iron. Suitable nutrient salts include MS salts (Murashige and Skoog (1962) Physiol. Plant 15:473–497), half strength MS, B5 (Gamborg et al. (1968) Exp. Cell Res. 50:151-158), White's (White (1934) Plant Physiol. 9:585-600), Kao's (Kao (1977) Mol. Gen. Genet. 150:225-230), KM (Kao and Michayluk (1975) Planta 126:105-110), and the like.

Suitable energy sources include sugars, such as glucose, maltose, sucrose, lactose, fructose, sucrose in combination with any of the other named sugars, or mannose. A preferred sugar is glucose at a level of about 5 to 50 g/l, preferably about 16 g/l, with molar equivalents of other sugars also being suitable.

The general pepper medium may include an auxin and/or cytokinin component. Any auxin, natural or synthetic, may be used, e.g., indoleacetic acid (IAA), naphthaleneacetic acid (NAA), 2,4-dichlorophenoxyacetic acid (2,4-D) and picloram. Mixtures of auxins may be employed e.g., IAA and NAA. The cytokinin may be selected from any of the known cytokinins, natural or synthetic, and may include, but is not limited to 6-benzylaminopurine (6-BA, also called $N^6$-benzyladenine), zeatin (ZEA), kinetin (KIN), isopentyladenine (IPA), and thidiazuron (TDZ). Mixtures of auxins and cytokinins may be employed e.g., IAA and 6-BA or NAA and KIN. Generally the auxin(s) will be present in an amount of about 0.05–10 mg/l, and cytokinin in an amount of about 0.1–25 mg/l.

Any of the known gibberellins may be included in the media (e.g., $GA_1$ through $GA_{13}$) with $GA_3$ being preferred. Generally the gibberellin will be present in an amount of about 0.1-50 mg/l.

Growth regulators (e.g. ABA) or combinations of growth regulators may also be included in the medium. A preferred growth regulator is an inhibitor of ethylene action, such as silver nitrate or silver thiosulfate. Generally silver nitrate or silver thiosulfate, when present, will be present in an amount of 1-100 µM preferably about 15 µM. Inhibitors of ethylene production may also be used.

Amino acids, such as glycine, may be employed in the general pepper medium as a nitrogen source. Other nitrogen sources include ammonium nitrate, potassium nitrate, and sodium nitrate. Various vitamin formulations can be included, e.g., MS vitamins, B5 vitamins, Km vitamins, or combinations of thiamine (0.5-10 mg/l, about 1 mg/l preferred), nicotinic acid (0.5-3.0 mg/l), inositol (10-1000 mg/l, about 1000 mg/l preferred), and pyridoxine (0.5-5.0 mg/l). For solid media, an appropriate amount of solidifying agent may be added to the mixture, e.g. agar or Gel-rite ®. 2-(N-Morpholino)ethanesulphonic acid (250-1000 mg/l, about 600 mg/l preferred) may be added as a buffer. In general, media pH should be in the range of about 5.2-6.5, preferably about 5.8. Other inorganic or organic elements or compounds may also be added (e.g., adenine sulfate at 5 to 200 mg/l, 20 mg/l preferred; and casein hydrolysate at 10 to 500 mg/l, 200 mg/l preferred).

Prior to cocultivation with the Agrobacterium cells, the pepper seed cotyledons or other explant materials preferably should first be sterilized. The sterilization medium should contain any substance effective against contaminating microorganisms and nontoxic to plants. Such compounds may include but are not limited to sodium hypochlorite, mercuric chloride, and alcohol. A preferred sterilization agent is commercial bleach (active ingredient is sodium hypochlorite) used at a concentration range of 10–50% of full strength. Surfactants (e.g. Tween ® 80) may be added to aid the wetting of the seeds by the sterilization medium. The seeds are sterilized by immersion in sterilization medium for 5 to 45 minutes (about 20 minutes preferred) with or without shaking on a rotary shaker at up to 200 rpm (about 50 rpm preferred). The sterilization medium is then removed and replaced with sterile distilled water. The sterile distilled water is then replaced with fresh sterile distilled water to insure that the sterilization medium is fully removed from the seeds. All subsequent manipulations should be done in such a way as to maintain sterility (e.g., in a laminar airflow hood).

The sterilized seeds are imbibed/germinated on germination medium, which is the same as the general pepper medium, lacking plant hormones (i.e., auxins and cytokinins). If expanded cotyledons are to be used as the explants, sufficient time should be allowed at a sufficiently high temperature (preferred is about 10 days at 28° C.) to allow the seeds to germinate. The cotyledons are then removed and dissected into sections (e.g., 3-4 sections preferred). If sections are being prepared for use in the transformation protocol, they should be dissected while submerged in the culture of the Agrobacterium strain to be used for cocultivation. After being dissected, the sections should be transfered to cocultivation medium, as set forth hereinafter.

If embryonic cotyledons are to be used (see section on type/source of explant), they should be excised from the seed coat and endosperm, and dissected into sections (e.g., 2-4 sections preferred). If sections are being prepared for use in the transformation protocol, they should then be dipped in the Agrobacterium culture, and transfered to cocultivation medium (described below). other types of explants (e.g., hypocotyl, leaves, roots) should be prepared for cocultivation similarly to the above by dissection into small (0.5 mm to 10 mm, preferably 1 mm to 5 mm, most preferably about 2 mm) sections. The dissection may be done while submerged in the Agrobacterium culture or the sections may be subsequently dipped into the Agrobacterium culture. The inoculated explants should then be transferred to the cocultivation medium.

The pepper explant material is combined with the Agrobacterium cells in a cocultivation medium as follows. Cocultivation medium is the same as the general pepper medium except that a virulence (vir) region induction compound is preferably included to induce the vir region of the Agrobacterium cells to enhance transformation efficiencies. Suitable vir induction compounds include acetosyringone (3',5'-dimethoxy-4'-hydroxyacetophenone, AS) at concentrations between 10–300 uM (100 uM preferred). Instead of AS, any phenolic compound known to the art can be used at comparable molar concentrations. See Bolten et el. (1986) Science 232:983–985.

In addition to the virulence induction compound, a preferred cocultivation medium according to the present invention will utilize glucose as the energy source, at about 5 to 50 g/l, (preferably at about 16 g/l), BA as the cytokinin (usually at 0.5–15 mg/l, preferably at 10 mg/l). Use of an auxin is optional; however, if any auxin is used, IAA is preferred at 0.1 to 50 mg/l (preferably about 1 mg/l). The use of MS salts is preferred. Abscisic acid may be present at 0.05 to 0.5 mg/l. Gibberellic acid (GA) may be present at 0.1 to 10 mg/l; preferably at 0.1 to 1 mg/l, and most preferably 0.1 mg/l.

A particularly preferred cocultivation medium for use with expanded cotyledon explants is 10 BI/AS, as set forth in the Experimental section hereinafter. A particularly preferred cocultivation medium for use with embryonic explants is 0.1GBI/AS, as set forth in the Experimental section hereinafter.

The explants are mixed with the Agrobacterium suspension cells at about $6 \times 10^7$–$6 \times 10^9$ cells/ml (preferably about $6 \times 10^8$ cells/ml) as prepared above. Preferably about 50 explants are used, and mixed with about 2 ml of Agrobacterium suspension cells. Explants are suspended in the Agrobacterium suspension for less than 1 minute. The explants are transferred to the cocultivation medium over which a sterile circle of filter paper has preferably been placed such that the explants are in contact with the filter paper rather than in contact with the cocultivation medium directly. Alternatively, the explants can be placed directly in contact with the cocultivation medium. Explants and Agrobacterium are cocultured (preferably in the dark) at 20–28C (preferably 24° C.) for 2–6 days (preferably 5 days). See Marton et al., (1979) Nature, 227:129.

Explants may be washed of excess Agrobacterium with a liquid medium (e.g. MS, B5) or water (preferably MS). Explants are mixed well with the liquid medium in a petri dish, on a shaker at about 30–100 rpm (preferably 60 rpm) at a ratio of about 10–30 (preferably about 20) explants to 25 ml of liquid medium. The liquid medium is replaced with 25 ml of the same liquid medium after 15 minutes, 1–5 times (preferably 3). Antibiotics may be included in the liquid medium to aid in removal of the Agrobacterium. Any anti-Agrobacterium antibiotic may be used. Preferred antibiotics are cefotaxime (200–1000 mg/l, preferably about 500 mg/l), vancomycin (100–500 mg/l, preferably about 100 mg/l), erythromycin (200–1000 mg/l), or amoxicillin (50–500 mg/l). Combinations of antibiotics may also be used. Most preferred is about 500 mg/l cefotaxime, and about 100 mg/l vancomycin. The explants are subsequently transferred to a selection/induction medium (see below), preferably with about 10 explants per 33 ml of medium.

The explant material is then transferred to an induction medium or selection/induction medium for shoot induction. The induction media are media with a composition sufficient to induce shoot formation. The selection/induction media, which are used with transformed explant material, additionally permit and maintain the selection process following the cocultivation protocol. These media are the same as the general pepper medium, except that the selection/induction medium also includes (a) an antibacterial antibiotic (same choices and concentrations as listed above for wash step, most preferred is about 500 mg/l cefotaxime and (b) a selection agent to permit selection of transformed shoots based on the type of plant selectable marker gene present in the Agrobacterium.

These media preferably contain a high concentration of a strong cytokinin (e.g., BA at 5–20 mg/l, about 10 mg/l preferred) when using expanded cotyledons and a moderate concentration (e.g., BA at 0.5 to 5 mg/l, about 1 mg/l preferred) when using embryonic cotyledons. These media also may contain an auxin (e.g., IAA at 0.1 to 10 mg/l, about 1 mg/l preferred) for use with expanded or embryonic cotyledons. Glucose is preferred at 16 g/l.

The selection/induction medium will usually further comprise an agent to select for transformed shoots. As described hereinabove, a marker gene(s) which is selectable and/or screenable in plants ("plant selectable marker") should be included in the T-DNA of the Agrobacterium strain which is used for cocultivation. Suitable marker genes include genes coding for resistance to the antibiotic spectinomycin (e.g., the aadA gene), the streptomycin phosphotransferase (SPT) gene coding for streptomycin resistance, the neomycin phosphotransferase (NPTII) gene encoding kanamycin resistance, the hygromycin phosphotransferase (HPT) gene coding for hygromycin resistance, or genes coding for resistance to the sulfonylurea-type herbicides (e.g., the acetolactate synthase (ALS) gene containing mutations leading to resistance to sulfonylurea-type herbicides, in particular the S4 and/or Hra mutations). The use of the mutant ALs genes is preferred.

If the marker is sulfonylurea resistance, the selection/induction medium should contain a sulfonylurea-type herbicide at an appropriate concentration (e.g. chlorsulfuron in the range of 20–1000 mg/l preferably about 20 to 100 mg/l most preferably about 50 mg/l). For selection of kanamycin-resistant pepper shoots which contain the NPTII gene, kanamycin should be included in the medium at 100–500 mg/l, preferred is about 300 mg/l. Spectinomycin-resistant shoots containing the aadA gene should be selected by inclusion of 200–1000 mg/l spectinomycin (about 500 mg/l preferred) in the medium.

A particularly preferred induction medium when using expanded cotyledons is 10BI, as set forth in the Experimental section hereinafter. A particularly preferred induction medium when using embryonic cotyledons is LGBI, as set forth in the Experimental section hereinafter. A particularly preferred selection/induction medium when using expanded cotyledon explants and the mutant ALS gene is 10BI/cscf, as set forth in the Experimental section hereinafter. A particularly preferred selection/induction medium when using embryonic cotyledon explants and the mutant ALS gene is 0.1GBI/cscf, as set forth in the Experimental section hereinafter.

For purposes of regeneration without transformation, the explant material is transferred to the induction medium immediately following its sterilization. The cultures are maintained at 20° to 30° C. (preferably about 24° to 28 C. most preferably about 26° C.) in the light or dark until shoot buds appear. If the cultures are maintained in the light the light intensity should be less than 3000 lux (preferred is about 2000 lux with about a 16 hour day, 8 hour night photoperiod). No particular photoperiod need be used. Shoot buds (small shoots) are generally visible within about 2 to 3 weeks of culture initiation. They are usually present in clumps of 10 to 100 shoot buds at the margin of the explant. During this time the explants generally swell and become green. Callus often also forms at the margin of the explants, however it is not associated with (i.e., it is separate from) the regenerating shoot buds.

Explants derived from cocultivation with Agrobacterium are transfered to the selection/induction medium following the cocultivation procedure. The cultures are maintained under the same conditions described above. The explants are maintained on this medium until shoot buds resistant to the selection ("putatively transformed shoots") are visible. These shoot buds are generally visible within 3 to 5 weeks of culture initiation at the margin of the explant, and may be present as single shoot buds or as clumps of shoot buds. During this time the explants may turn brown or black and necrotic due to the presence of the selective agent. The putatively transformed shoots produced on kanamycin, spectinomycin, and chlorsulfuron-containing media are completely green. Occasionally, calli will form at the margin of the explants on selection/induction medium as well. These calli generally continue to grow indicating that they are probably composed of transformed cells as well.

Within 1 to 3 weeks of when they are visible (2 weeks preferred), the shoot buds generated on the induction medium, and the explant to which they are still attached are transferred to an elongation medium. Putatively transformed shoot buds, i.e., those generated on the selection/induction medium, should be initially transfered to an elongation/selection medium. The elongation/selection medium is the same as the elongation medium except that plant selection agents and antibacterial antibiotics are included to insure that the Agrobacteria are completely eliminated and that the regenerated shoots are composed of transformed cells.

The elongation medium is the same as the induction medium except that the plant hormones are preferably altered by omitting the auxin and altering the cytokinin concentration (e.g., by altering the BA concentration to 1 to 10 mg/l, preferably about 4 mg/l). Also included in the elongation medium are the compounds inositol, silver thiosulfate, casein hydrolysate, and adenine sulfate. A gibberellin, such as $GA_3$ ay should be added to this medium at a concentration of 0.1 to 50 mg/l, preferably 0.1 to 25 mg/l, about 10 mg/l preferred. Elongating cultures are maintained in environmental conditions (temperature and light/day length) which are the same as for induction or selection/induction. The shoot buds expand and elongate under these conditions. For purposes of regeneration, these cultures should be transfered to fresh elongation medium every 1 to 10 weeks (about 2 weeks preferred). After 3 to 10 weeks on elongation medium (about 4 weeks preferred), the shoot buds should be excised from the original explant with a scalpel and transferred to fresh elongation medium or preferably to a second elongation medium lacking plant hormones but containing additional thiamine (0.1 to 10 mg/l, preferably about 1 mg/l).

In the case of transformed shoots/explants, after the shoots/explants have been on the elongation/selection medium for 3 to 5 weeks (4 weeks preferred), the excised shoots should be transferred to a second elongation/selection medium. This medium has the same composition as the elongation/selection medium but lacks the antibacterial antibiotic.

Shoots should be maintained on elongation medium or the second elongation medium (or for transformed shoots/explants, elongation/selection medium or second elongation/selection medium) with continued transfers every 2 weeks to 3 months, (about once per month preferred) until the shoots are at least 1 cm high and are displaying evidence of normal morphological development (i.e., they have normalized). Normal morphological development can be recognized by the presence of a distinct growing point on the stem and the regular emergence of new leaves. The process of elongation may take from about 1 to 8 months.

A particularly preferred media for shoot elongation is B4, as described in detail in the Experimental section hereinafter. Particularly preferred shoot elongation/selection media are B4/cscf and B4/cs, as described in detail in the Experimental section hereinafter. A preferred second elongation medium is MSOT, as described in detail in the Experimental section hereinafter. A particularly preferred second elongation/selection medium is MSOT/cs, as described in detail in the Experimental section hereinafter.

Shoots may root (i.e., have roots emerge from the lower part of the shoot) on the elongation or elongation/selection medium. If such rooted plants are already normalized, the rooting/normalizing stage described below is unnecessary. If the shoots are large (5 to 15 mm, 10 mm preferred) and have not yet rooted, they may be transfered to rooting medium to induce rooting.

Rooting medium is the same as the general pepper medium with an auxin included (e.g., NAA at a concentration of 0.05 to 1 mg/l, about 0.1 mg/l preferred). The cultures on rooting medium should be maintained under the same environmental conditions as for induction. Rooting of cultures for regeneration and for transformation/regeneration is the same. Rooted plants may be transferred to a greenhouse if they have rooted and normalized. If the plants did not normalize on the shoot elongation medium, they should now be normalized (note that plants may root which have not normalized).

A particularly preferred rooting medium is OMSSN, as described in the Experimental section hereinafter.

Particular methods for confirming shoot transformation derived from explant material treated by the method of the present invention are known in the art. For instance, confirmation may be accomplished by growing plants, growing callus or growing roots in a medium containing a selection agent. The presence of a reporter gene may also be demonstrated to confirm transformation, e.g., by GUS β-glucuronidase (GUS) or luciferase (luc) assays, if there is included in the T-DNA of the Agrobacterium a fragment encoding a β-glucuronidase or luciferase gene, respectively, by using procedures known to the art. See, for example, Jefferson et al. (1986) Proc. Natl. Acad. Sci. 83:8447–8451 (GUS) and Ow et al. (1986) Science 234:856–859 (luc).

The DNA fragment transfered from the Agrobacterium to the plant genome may also be detected by DNA detection means using procedures known in the art. These include Polymerase Chain Reaction (PCR), restriction enzyme digestion, and Southern blot hybridization. Northern blot hybridization or any method suitable for detection of mRNA transcripts from the transforming DNA, and western blots or any other method suitable for detection of proteins ultimately translated from the transforming DNA, may also be used to confirm the transformed nature of selected individuals. See Maniatis regarding detection assays.

Genetic variation among plants regenerated from in vitro cell cultures has been reported. See Evans et al. (1986) Biotechnology 4:528-532. This variation has been attributed to mutation, gross chromosomal changes (translocation, inversion, deletion) and polyploidy. In order to identify a polyploid (e.g., tetraploid) plant among plants regenerated using the invention, the number of chloroplasts in leaf stomates are determined according to I. Ho et al. (1990) Plant Breeding 105:203-210. A diploid pepper plant has about 15-25 chloroplasts per stomate and a tetraploid pepper plant has about 28-37 chloroplasts per stomate. The frequency of appearance of mutations may be enhanced by the addition of mutagens (e.g., ethylmethane sulfonate) to the culture media. The frequency of appearance of polyploids (e.g., tetraploids) may be enhanced by the addition of compounds known to inhibit spindle formation (e.g., colchicine) to the media.

Tetraploidy is verified by counting the chromosomes in the root tip cells of progeny plants according to R. A. Morrison et al. Supra. A diploid pepper plant has 24 chromosomes while a tetraploid pepper plant has 48 chromosomes.

The following examples are offered by way of illustration and not by way of limitation.

EXPERIMENTAL MATERIALS

| Abbreviations/Names | Source/Reference |
|---|---|
| aadA; Aminoglycoside-3" Adenyltransferase Gene | Svab et al. (1985) Pl. Mol. Biol. 14:197-205 |
| Adenine hemisulfate | Sigma Chemical Co., St. Louis, MO, USA |
| AS; Acetosyringone | Aldrich Chemical Co., Milwaukee, WI, USA |
| B5 Salts and Vitamins | Gamborg et al. (1968) Exp. Cell Res. 50:151-158 |
| BA (6-BA); 6-Benzlaminopurine | Sigma Chemical Co., St. Louis, MO, USA |
| Casein hydrolysate | Sigma Chemical Co., St. Louis, MO, USA |
| Carbenicillin | Duchefa, Haarlem, Holland |
| Chlorsulfuron | E. I. DuPont de Nemours & Co., Wilmington, DE, USA |
| Cefotaxime | Calbiochem Corp., La Jolla, CA, USA |
| Colchicince | Sigma Chemical Co., St. Louis, MO, USA |
| 2,4-D; 2,4-Dichlorophenoxyacetic Acid | Sigma Chemical Co., St. Louis, MO, USA |
| $GA_3$; Gibbarellic acid | Sigma Chemical Co., St. Louis, MO, USA |
| Gel-rite ® | Scott Lab. Inc., Warwick, RI, USA |
| Glucose | |
| GUS; β-glucuronidase | Jefferson et al. (1986) Proc. Natl. Acad. Sci. USA 83:8447-8451 |
| HPT; Hygromycin Phosphotransferase Gene | van den Elsen et al. (1985) Pl. Mol. Biol. 5:299-302 |
| Hygromycin | Calbiochem Corporation, La Jolla, CA, USA |
| IAA; Indole-3-acetic acid | Sigma Chemical Co., St. Louis, MO, USA |
| Inositol | Sigma Chemical Co., St. Louis, MO, USA |
| Kanamycin | Sigma Chemical Co., St. Louis, MO, USA |
| MES, 2-N Morpholinoethanesulfonic Acid | Sigma Chemical Co., St. Louis, MO, USA |
| MS Salts | JRH Bioscience, Lenexa, KS, USA |
| NAA, Naphthaleneacetic acid | Sigma Chemical Co., St. Louis, MO, USA |
| PCR; Polymerase chain reaction | Saiki et al. (1985) Science 230:1350-1354 |
| Silver thiosulfate | Prepared fresh by mixing an equal part of a 12 mM solution of silvernitrate (Sigma) into a 56 mM solution of sodium thiosulfate (Sigma). |
| Sodium hypochlorite bleach | All Pure Chemical Co., Tracy, CA, USA |
| Spectinomycin dihydrochloride | Sigma Chemical Co., St. Louis, MO, USA |
| Tetracycline | Sigma Chemical Co., St. Louis MO, USA |
| Thiamine-HCl | Sigma Chemical Co., St. Louis, MO, USA |
| Triton, TritonX-100 | Sigma Chemcial Co., St. Louis, MO, USA |
| Tween ® | ICI United States, Inc., Wilmington, DE, USA |
| Vancomycin | Sigma Chemical Co., St. Louis, MO, USA |
| Zeatin | Sigma Chemical Co., St. Louis, MO, USA |

MEDIA COMPOSITIONS

| Minimal A | preferred | range |
|---|---|---|
| potassium phosphate dibasic | 10.5 g/l | 5-20 g/l |
| potassium phosphate monobasic | 4.5 g/l | 2-8 g/l |
| ammonium sulfate | 1.0 g/l | 0.5-3 g/l |
| sodium citrate dihydrate | 0.5 g/l | 0-2 g/l |
| magnesium sulfate heptahydrate | 247 mg/l | 0-1000 g/l |
| glucose | 2.0 g/l | 1-30 g/l |

The pH should be 5-7.5, preferrably 5.5. The medium is used following sterilization by filtration.

OMSG

| | |
|---|---|
| MS salts | 1X |
| B5 vitamins | 1X |
| Glucose | 16 g/l |
| MES | 600 mg/l |
| Gel-rite ® | 2.5 g/l |
| pH | 5.8 |

OMSG/cs

OMSG + 50 μg/l chlorsulfuron

10BI

| | |
|---|---|
| MS salts | 1X |
| B5 vitamins | 1X |
| Glucose | 16 g/l |
| MES | 600 mg/l |
| BA | 10 mg/l |
| IAA | 1 mg/l |
| Gel-rite ® | 2.5 g/l |
| pH | 5.8 |

10BE/AS

10BI + 200 μM acetosyringone (As)

10BI/cscf

10BI + 50 μg/l chlorsulfuron + 500 mg/l cefotaxime

.1GBI

| | |
|---|---|
| MS salts | 1X |
| B5 vitamins | 1X |
| Glucose | 16 g/l |
| MES | 600 mg/l |
| BA | 1 mg/l |
| IAA | 1 mg/l |
| $GA_3$ | 0.1 mg/l |
| Gel-rite ® | 2.5 g/l |
| pH | 5.8 |

.1BGI/AS

.1GBI + 200 μM acetosyringone (As)

-continued

.1GBI/cscf
.1GBI + 50 μg/l chlorsulfuron + 500 mg/l cefotaxime

B4
| | |
|---|---|
| MS salts | 1X |
| B5 vitamins | 1X |
| Glucose | 16 g/l |
| MES | 600 mg/l |
| inositol | 1 mg/l |
| adenine sulfate | 20 mg/l |
| casein hydrolysate | 200 mg/l |
| BA | 4 mg/l |
| GA$_3$ | 10 mg/l |
| silver thiosulfate | 15 μM |
| Gel-rite ® | 2.5 g/l |
| pH | 5.8 |

B4/cs
B4 + 50 μg/l chlorsulfuron

B4/cscf
B4/cs + 500 mg/l cefotaxime

MSOT
| | |
|---|---|
| MS Salts | 1X |
| MS Vitamins | 1X |
| Sucrose | 30 g/l |
| Inositol | 1 g/l |
| Thiamine HCl | 1 mg/l |
| Gel-rite ® | 2.5 g/l |
| pH | 5.8 |

MSOT/cs
MSOT + 50 mg/l chlorsulfuron

OMSSN
| | |
|---|---|
| MS salts | 1X |
| B5 vitamins | 1X |
| Sucrose | 30 g/l |
| MES | 600 mg/l |
| NAA | 0.1 mg/l |
| Gel-rite ® | 2.5 g/l |
| pH | 5.8 |

EXAMPLES

I. Transformation Examples

Example 1

1.1. Explant Source

Approximately 300 mature seeds of *Capsicum annuum* cv.s California Wonder (Northrup King Co., Gilroy, Calif.) were surface sterilized by briefly dipping them in 70% ethanol followed by soaking them in a solution of 50% of full strength sodium hypochlorite for 15 minutes on a rotary shaker set at 100 rpm. The seeds were then rinsed with sterile double distilled water three times and transfered to magenta boxes containing 50 ml of sterile OMSG medium. The seeds were planted at 25 seeds per box. The boxes were incubated for 13 days in the dark at 28° C. during which time the seeds germinated.

1.2. Preparation of *Agrobacterium* inoculum

*Agrobacterium tumefaciens* strain LBA4404 (Hoekema, 1983, Nature 303:179-181) was used for cocultivation. The strain used for transformation (LBA4404/p5T35AD) contained the binary vector p5T35AD in which the Cauliflower Mosaic Virus 35S promoter (Odell et al (1985) Nature 313:810–812) drives a double mutant form of the ALS gene which confers resistance to the herbicide chlorsulfuron (Lee et.al., EMBO J. 7:1241-1248, 1987). A second strain of *Agrobacterium tumefaciens* strain LBA4404 (eLBA) which contained no binary vector was used for control cocultivations. The Agrobacterium cells were maintained on Minimal A plates. The plates used for culturing LBA4404/p5T35AD were supplemented with 50 mg/l kanamycin. The plates use for culturing eLBA were not supplemented. Overnight suspensions of each bacterial strain were initiated by the addition of a single bacterial colony to 5 ml of liquid Minimal A medium (supplemented with 100 mg/l kanamycin for LBA4404/p5T-35AD) in a sterile test tube. The tubes were incubated overnight on a rotary shaker set at 150 rpm in continuous light at 28° C. Inoculum densities of approximately $6 \times 10^8$ bacteria per ml were used.

1.3. Preparation of Explants

The cotyledons from 281 of the sterile seeds described in Section 1.1 were removed and each entire cotyledon was cut into approximately 3 or 4 sections each with a sterile scalpel. The sections were submersed in liquid (i.e. lacking the Gel-rite ®) OMSG medium in a sterile 150×15 mm petri dish prior to inoculation.

1.4. Inoculation and Cocultivation of Explants

The liquid OMSG medium was removed by pipetting and 720 of the explants were inoculated with the LBA4404/p5T35AD bacterial strain by pipetting the entire suspension (5 ml) onto the explants (transformation explants). Two hundred and forty of the remaining explants were treated the same as the above explants except that they were cocultivated with the eLBA bacterial strain (control explants). Both the control and the transformation explants were transferred individually on the tip of a sterile scalpel from the bacterial suspensions to 10BIAS medium for cocultivation. They were cocultured in the dark for 3 days. The first 16 hours of the coculture period was at 28° C. and the remainder was at 24° C.

1.5 Selection/Induction of Regenerated Shoot Buds

Following the cocultivation period, all explants were washed in OMSG medium supplemented with 500 mg/l carbenicillin, 500 mg/l cefotaxime, and 500 mg/l vancomycin. The explants were washed briefly, followed by a 30 minute wash, followed by a 1 hour wash, followed by a 20 hour wash, followed by a final brief wash (total=5 washed). The washed explants were transferred to selection/induction medium, specifically 20 explants per plate of 10BI/cscf but containing 500 mg/l carbenicillin and lacking cefotaxime. Plates were wrapped with parafilm and cultured in the dark at 28° C. After 24 days, the explants were transfered to fresh medium of the same composition as before, but supplemented with 15 μM silver thiosulfate.

1.6. Elongation/Selection of Regenerated Shoots

Fourteen days later (total=5½ weeks), the explants (with shoot buds) were transferred to 5BSTS/csc medium (OMSG/cs medium supplemented with 5 mg/l BA, 500 mg/l carbenicillin, and 15 μM silver thiosulfate) for shoot elongation. At this point, the cultures were moved to culture conditions of 28° C., 500 Lux light, and 16 hour photoperiods. Nineteen days later (total=8 weeks), the explants were transferred to fresh media of the same composition. One week later, (total=9 weeks) the cultures were moved (without transfer) to the same conditions as before but with a light intensity of 2500 Lux. Twenty days later (total=12 weeks), the shoot buds which had formed were removed from the original explants by cutting with a scalpel, and transfered to OMSG/cs medium supplemented with 15 μM silver thiosulfate and 500 mg/l carbenicillin. Two months later (total=5 months), the shoot buds were transfered to MSOT supplemented with 50 μg/l chlorsulfuron.

1.7. Rooting

Six weeks later (total=6½ months), five shoots were still alive and in the process of elongating and normalizing. These shoots were transfered to OMSSN media for rooting. Two months later (total=8½ months), the two shoots which had rooted were transferred to fresh OMSSN media lacking the NAA. One month later (total=9½ months), these two plants appeared to have normalized and were removed from culture and transfered to a greenhouse.

1.8. Assays to Show Transformation

The five transformed shoots which were able to grow on the selection medium were analyzed by PCR (see PCR Protocols A Guide to Methods and Applications: Innis, M. A.; Gelfand, D. H.; Sninsky, J. J. White, T. J. Academic Press 1990). Using 16-meroligonucleotides designed to amplify a 438 bp fragment of the introduced ALS gene, genomic DNA from the 5 shoots was thermocycled for 40 cycles followed by resolution of the resulting amplified DNA fragments on an agarose gel. The expected fragment was detected in all 5 shoots. The transformation efficiency (number of confirmed transformed shoots divided by the total number of inoculated explants) was $(5/720) \times 100 = 0.7\%$. Two of the five shoots described above subsequently rooted on OMSSN medium. These two plants were further analyzed by using a callusing assay. Small portions of each expanded leaf on the regenerated plants were cut off and placed on 10BI/cscf medium. Non-inoculated, non-selected control explants were also placed on the same medium. The plates were cultured at 28° C. in the dark for one month. The explants from transformed plants formed callus all the way around the perimeter of each explant, whereas the control explants formed no callus and became necrotic. This further demonstrates the transformed nature of these two plants.

Seeds produced by self-pollination were collected from one of the plants and assayed for the transmission of the chlorsulfuron-resistance characteristic to the next generation. These seeds were harvested in a laminar flow hood in such a way as to maintain their natural axenic condition and transferred to OMSG/cs medium. Of the 16 seeds that germinated, 14 produced roots that penetrated far into the agar medium and 2 did not penetrate the medium at all. All of 20 non-transformed seeds which were treated identically produced roots which did not penetrate into the medium at all. This segregation ratio is consistent with the plant being transformed at a single genetic locus or at 2 genetic loci.

Example 2

This example was performed as in Example 1 except that the pepper variety used was the bell-type pepper Dulce Italiano (Clause semences professionnelles, CEDEX, FRANCE). The cocultivation was for 4 days at a constant 24° C. and the wash solution was as before except that the vancomycin concentration was changed to 100 mg/l. The cocultured explants were washed briefly, followed by three 1 hour washes, followed by an overnight wash, followed by a brief wash. After 21 days of culture, no shoots were seen on the 240 explants cocultivated with eLBA, but 2 shoots were seen on the 720 explants cocultivated with p5T35AD. Transfer to the silver thiosulfate-containing medium was done after 23 days. Two weeks later, elongation/selection of the shoots on 5BSTS/csc was begun as in example 1. Four weeks later the shoots were excised from the explants and transferred to fresh 5BSTS/csc medium. Two and one half months later, the shoots were transferred to the fresh 5BSTS/csc medium but lacking the carbenicillin. One month later the shoots were transferred to MSOT medium supplemented with 50 μg/l chlorsulfuron. One and one half months later the shoots were transferred to OMSSN medium for rooting. At this point DNA was isolated from a small leaf sample from each of the 2 shoots and a PCR reaction was run. The expected fragment was detected from both of the shoots, thus confirming the transformed nature of these shoots. These shoots are taken to a greenhouse and grown to whole fertile plants as described in Example 1.

Example 3

This example was performed as in Example 2 except that cotyledons from 9 day old seedlings of the Vegisweet pepper variety 89300-1 were used, the cocultivation was for 5 days, and the washing protocol was further modified as follows: the cocultivated explants were washed twice briefly with the antibiotic mixture followed by a final wash with liquid OMSG medium and then immediately transferred to culture media. The culture medium used for selection/induction in this example was unmodified 10BI/cscf.

Following 24 days of culture the explants were evaluated for shoot bud formation with the following results: 43 out of 200 explants cocultivated with p5T35AD had shoot buds and 0 out of 120 explants cocultivated with eLBA had shoot buds. The explants were transferred to fresh 10BI/cscf media at this time and were incubated for an additional 16 days. Re-evaluation for shoot bud formation at this time showed that 54 out of the 200 explants cocultivated with p5T35AD had formed shoots (transformation efficiency=27%) whereas still no shoots were seen on the controls. At this time all shoots and explants were transferred to B4/cscf2 medium (B4/cscf with the cefotaxime concentration reduced to 250mg/l). Three weeks later, the shoots were removed from the explants and transferred to fresh B4/cscf2 medium. Two weeks later, 17 of the shoots had elongated and were transferred to MSOT/cs. These shoots are transferred to OMSSN for rooting and finally transferred to a greenhouse for growth and seed production.

Confirmation that the shoots described above were transformed was done by callusing assay. Forty one days after the cocultivation was begun, small pieces of leaves from each of 6 transformed shoot buds were excised with a scalpel and transferred to a callusing medium (OMSG/cs supplemented with 1 mg/l NAA, 0.17 mg/l, 2,4-D, 0.4 mg/l Zeatin, and 250 mg/l cefotaxime). Six days later, 8 additional shoot buds were assayed by callusing in the same way. All 14 of the shoot buds assayed in this way produced prolific callus whereas explants from the control (i.e. non-transformed) shoot buds died.

Example 4

This example was performed as in Example 2 except that a strain of *A. tumefaciens* LBA4404 which contained the binary vector pSLJ1911 was used for cocultivation. In this strain, two Cauliflower Mosaic Virus 35S promoters are used to drive the neomycin phosphotransferase (NPTII) gene (Beck et.al., GENE 19:327-336, 1982) and the b-glucuronidase (GUS) gene (Jefferson et.al., PNAS 83:8447-8451). The NPTII gene confers resistance to the antibiotic kanamycin and the GUS gene provides an easily screenable product (reporter gene) which can be used to assay plants to confirm that they are transformed. Bacterial strains lacking a binary plasmid (eLBA) or containing pSLJ1911 were grown and used in the same way as the strains described in example 1 except that all media used for the strain containing pSLJ1911 contained 5 mg/l tetracycline and no kanamycin. The cocultivation period was 3 days at a constant 24° C. The washing solution of example 1 was combined with the washing protocol of example 2. The cocultivated explants were transferred to the selection-/induction medium 10BI supplemented with 500 mg/l carbenicillin and kanamycin at 100, 250, and 500 mg/l and incubated in the conditions described in example 1 for one month. At this time the cultures were evaluated for shoot bud formation (results provided below):

| KANAMYCIN CONCENTRATION | PLASMID (# shoot buds/# explants) | |
| --- | --- | --- |
| | eLBA | pSLJ1911 |
| 100 mg/l | 10/50 | 14/140 |
| 250 mg/l | 1/50 | 1/140 |
| 500 mg/l | 0/50 | 1/140 |

A GUS assay was performed on the two shoot buds which appeared on the pSLJ1911-cocultivated explants which were incubated on 250 and 500 mg/l kanamycin. The shoot bud on 250 mg/l turned a dark blue indicating that it was transformed, however the shoot bud on 500 mg/l kanamycin appeared faintly blue indicating it may or may not have been transformed. The remainder of the shoots were not taken through the protocol to get whole plants.

Example 5

This example was performed as in Example 4 except that the washing solution and washing protocol of Example 2 were used. The cocultivated explants were transferred to selection/induction medium as in example 4 except that the media contained 50, 100, 200, or 300 mg/l kanamycin. The cultures were evaluated for shoot bud formation following 3½ weeks of incubation (results provided below):

| KANAMYCIN CONCENTRATION | PLASMID (# shoot buds/# explants) | |
| --- | --- | --- |
| | eLBA | pSLJ1911 |
| 50 mg/l | 17/100 | 26/320 |
| 100 mg/l | 1/100 | 15/320 |
| 200 mg/l | 1/100 | 7/320 |
| 300 mg/l | 0/100 | 2/320 |

One week after these results were gathered, all explants were transferred to fresh media of the same composition as they were originally on. At the same time, the cultures were transferred to conditions of 28° C. and 2500 Lux light with a 16 hour photoperiod. Approximately 2 months later the cultures were again transferred to fresh plates as before.

Approximately six weeks later (four months after the experiment was started), a GUS assay was performed on 13 of the 26 pSLJ1911-cocultivated shoots which formed on 50 mg/l kanamycin. All of the shoots showed no blue reaction indicating that they were probably escapes. Similarly, GUS assays were done on 8 of the 15 shoots which formed on 100 mg/l kanamycin and 1 of the 7 shoots which formed on 200 mg/l kanamycin. No blue reaction was seen in these shoots also. Both of the shoots which formed on 300 mg/l kanamycin were GUS assayed as well. One of these shoots showed a deep blue reaction throughout the shoot indicating that it was fully transformed. The other shoot showed no blue reaction, however, some callus that was adhering to the base of this shoot did stain deep blue. This demonstrates that kanamycin-resistant, transformed shoots can be produced by the above procedure. The shoots which are not sacrificed for GUS staining are carried through the procedure of elongation and normalization followed by growth, maturation, and seed production in a greenhouse.

Example 6

This example was performed as in Example 2 except that a strain of A. tumefaciens LBA4404 which contained the binary vector pWTT2039 was used for cocultivation. In this strain, three Cauliflower Mosaic Virus 35S promoters are used to drive the hygromycin phosphotransferase (HPT) gene (Gritz and Davies, GENE 25:179-188, 1983), the β-glucuronidase gene, and the aadA gene (Chinault et. al., Plasmid 15:119-131, 1987). The HPT gene confers resistance to the antibiotic hygromycin, and the aadA gene confers resistance to the antibiotic spectinomycin. Bacterial strains lacking a binary plasmid (eLBA) and containing pWTT2039 were grown and used in the same way as the strains described in example 1 except that all media used for the strain containing pWTT2039 contained 20 mg/l gentamycin and no kanamycin.

The cocultivation period was 3 days at a constant 24° C. The explants were briefly washed twice with the washing solution of example 2, then they were transferred to a selection and medium of 10BI supplemented with 500 mg/l spectinomycin and 500 mg/l of either carbenicillin or cefotaxime. Following 23 days of culture, the explants were transferred to fresh media of the same composition as they were originally on. After an additional 15 days of culture (total = 5½ weeks), the cultures were transferred to light as in example 5. At this point it was noted that some of the explants which had been cocultivated with the strain containing pWTT2031 had shoot buds forming. Three days later, the explants were transferred to B4 or 5B5AN (the same as OMSG but supplemented with 5 mg/l BA and 5 mg/l silver nitrate) medium, each supplemented with 500 mg/l spectinomycin and returned to the same growing conditions. Following an additional 1 month of incubation under these conditions, the explants were evaluate for shoot bud formation. These results are provided below:

| COUNTER-SELECTION ANTIBIOTIC | ELONGATION MEDIUM | PLASMID (# shoot buds/# explants) | |
| --- | --- | --- | --- |
| | | eLBA | pWTT2039 |
| carbenicillin | B4 | 0/120 | 1/360 |
| carbenicillin | 5B5AN | 0/120 | 3/360 |
| cefotaxime | B4 | 0/120 | 8/360 |
| cefotaxime | 5B5AN | 0/120 | 6/360 |

It was noted that the 14 shoot buds which were on cefotaxime were better developed than the 4 on carbenicillin. At this time, the 18 shoot buds were excised from the explants and all were transferred to B4 medium supplemented with 500 mg/l spectinomycin. These were returned to the same growth conditions. Six weeks later, one of the shoots (cefotaxime counterselected, incubated on 5B5AN) was transferred to OMSSN medium from which the NAA was omitted. Three weeks later (total=4 months) this shoot was split into two shoots and was transferred to OMSSN medium for rooting. At about this time, a small portion of a leaf from each of these plants was assayed for GUS activity and found to stain a dark blue indicating that they were transformed.

After a total time of 6 months from when the transformation was done, the shoots had developed roots and were transferred to OMSSN medium lacking the NAA. These rooted shoots are transferred to the greenhouse for growth to maturity and seed production.

Example 7

This example was performed as in Example 6 except that the pepper variety California Wonder was used. The washed explants were transferred to 10BI medium supplemented with 500 mg/l cefotaxime and 500 mg/l spectinomycin for selection/induction. Half of the plates were incubated in the same cultural conditions as in example 6 (dark), and half were incubated in the same conditions except that they were incubated in about 2500 Lux of light with 16 hour photoperiods. Transfer to fresh media was done after 21 days. After a total of 6 weeks, the dark-incubated cultures were transferred to the lighted conditions described above.

Four days later, all cultures were transferred to B4 medium supplemented with 500 mg/l spectinomycin and 250 mg/l cefotaxime and returned to the same growth conditions. Following a total time (since the experiment was begun) of 2 months, shoot buds were noted in 1 of 150 explants which had originally been dark incubated, and 2 of 180 explants which had been continuously light incubated. Two and one half weeks later, one of the continuously light incubated shoots was transferred to OMSSN medium lacking the NAA. This shoot was assayed for GUS activity twice, once 3 months after the experiment was begun, and once 4 months later. Both of these assays were done by removing a small portion of a leaf for the assay. The leaf pieces turned dark blue in both of these assays indicating that the plant is transformed. This plant is transferred to the greenhouse for growth to maturity and seed production.

II. Regeneration Examples

Example 8

8.1. Explant Source

Approximately 100 mature seeds each of capsicum annuum cv.s California Wonder (Northrup King Co., Gilroy, Calif.) and PI 178849 (PI lines of Capsicum southern Regional Plant Introduction Station, Griffin, Ga., U.S.A.) were sterilized and rinsed as in example 1. These seeds were left in the final rinse of distilled water at room temperature with shaking (50 rpm) for 4 days.

8.2. Preparation of Explants

The embryonic cotyledons were dissected out of the seeds with a scalpel under magnification provided by a dissecting microscope. The embryonic cotyledons were removed by cutting the seeds transversely into 2 equal disks and then pulling the bisected embryo out of the endosperm with a sterile forceps. The radicle end of the embryo was excised and discarded, and the embryonic cotyledons were cut into 2 to 3 sections each.

8.3. Induction of Shoot Buds

The embryonic cotyledon pieces from 20 seeds were transferred to each of the following media: 10BI, BIA (the same as 0.1GBI but lacking the $GA_3$ and supplemented with 0.264M ABA), and PP4 (the same as B4 but lacking the $GA_3$ and silver thiosulfate and supplemented with 8 mg/l IAA). Plates containing the explants were wrapped with parafilm and transfered to a chamber set to maintain 28° C. with 16 hour photoperiods of 500 Lux light. Following about 2½ weeks of incubation, the experiment was evaluated for shoot bud formation. The number of explants producing shoot buds over the total number of explants tested was as follows:

CALIFORNIA WONDER: 10BI-13/20; PP4-15/20; BIA-5/5

PI 178849: 10BI-19/20; PP4-19/20; BIA-13/20

8.4. Elongation and Rooting of Regenerated Shoots

Three days after the explants were evaluated for shoot bud formation (above), the explants with shoot buds were segmented into approximately equal portions, each with approximately equal numbers of shoot buds. These were then portioned onto three different shoot elongation media; B4, OMSSN, and 5B5AN (the same as OMSG but supplemented with 5 mg/l BA and 5 mg/l silver nitrate). Following a 3 week incubation in the same environmental conditions as for shoot induction, the all shoots were excised from the original explants and transferred to one of three secondary elongation/rooting media for further elongation and rooting of the shoots (MSOT, MSOG, and OMSSN). The cultures were incubated as before for an additional 4½ weeks (total time from initiation of cultures was about 2½ months). At this time the cultures were evaluated for normal shoots. The following table provides the results of this experiment (the results from the three secondary elongation/rooting media were averaged):

| INITIA-TION MEDIUM | ELONGA-TION MEDIUM | FREQUENCY OF NORMALIZATION (# NORMAL/# EXPLANTS) | |
|---|---|---|---|
| | | CALIF. WONDER | PI 178849 |
| 10BI | B4 | 30/20 (1.5) | 108/52 (2.1) |
| | 5B5AN | 8/8 (1.0) | 16/21 (0.8) |
| | OMSSN | 0/6 (0.0) | 5/11 (0.4) |
| BIA | B4 | 3/13 (0.2) | 22/13 (1.7) |
| | 5B5AN | 0/7 (0.0) | 5/6 (0.8) |
| | OMSSN | 0/9 (0.0) | NO DATA |
| PP4 | B4 | 24/45 (0.5) | 46/30 (1.5) |
| | 5B5AN | 6/26 (0.2) | 17/22 (0.8) |
| | OMSSN | 0/9 (0.0) | 1/13 (0.1) |

Rearranging the data of this table shows that the mean number of shoots per explant portion when only the elongation medium is considered and other factors are averaged is:

B4=233/146 (1.6)

5B5AN=52/90 (0.6)

OMSSN=6/48 (0.1)

These results demonstrate that the $GA_3$-containing B4 medium is superior to the others for shoot normalization and that OMSSN is inferior.

8.5. Rooting

The normalized shoots which were produced above are transferred to additional rooting medium (OMSSN) if they have not formed roots on one of the above media and are finally planted in a greenhouse for growth to maturity and seed production.

Example 9

9.1. Explant Source

Explants were obtained the same as in Example 8 except that the varieties Super Red Pimiento (Stokes Seed CO, Buffalo, N.Y.), 89300-1 (DNAP, Cinnaminson, N.J.), 89288-2 (DNAP, Cinnaminson, N.J.), and Golden CalWonder (Holmes Seed CO, Canton Ohio) were used and seeds were left in the final rinse overnight rather than for 4 days.

9.2. Preparation of Explants

The procedure of Example 8 was followed.

9.3. Induction of Shoot Buds

Shoot buds were induced in the same way and on the same three media as in Example 8 except that the explants were evaluated for shoot bud formation after 2 weeks of incubation. The number of explants producing shoot buds over the total number of explants tested was as follows:

SUPER RED PIMIENTO: 10BI-9/20; PP4-9/20; BIA-18/20
89300-1: 10BI-6/15; PP4-8/20; BIA-12/20
89288-2: 10BI-9/20; PP4-11/20; BIA-12/20
GOLDEN CALWONDER: 10BI-8/20; PP4-8/20; BIA-14/20

Explants from these younger seeds formed shoot buds on BIA better than on the other media.

9.4. Elongation and Rooting of Regenerated Shoots

Shoot buds were elongated and rooted the same way as in Example 8 except that explants were portioned onto only 2 shoot elongation media (B4 and 5B5AN) and the transfer was done two weeks after evaluation. Excision and transfer to the secondary elongation/rooting medium was done 2 weeks later and only B4 was used as a secondary elongation/rooting medium. These cultures were incubated as before for an additional 5 weeks followed by evaluation (total time from initiation of cultures was about 2½ months). The following table provides the results of this experiment:

| INIT. MEDIA | ELONG. MEDIA | FREQUENCY OF NORMALIZATION (# NORMAL/# EXPLANTS) | | | |
|---|---|---|---|---|---|
| | | Super Red Pimiento | Golden CalWonder | 89288-2 | 89300-1 |
| 10BI | 5B5AN | 6/10 (0.6) | 27/10 (2.7) | 20/10 (2.0) | NO DATA |
| | B4 | 15/10 (1.5) | 39/10 (3.9) | 89/10 (8.9) | NO DATA |
| BIA | 5B5AN | 1/10 (0.1) | 20/10 (2.0) | 35/10 (3.5) | 18/10 (1.8) |
| | B4 | 7/10 (0.7) | 61/10 (6.1) | 59/10 (5.9) | 19/10 (1.9) |
| PP4 | 5B5AN | NO DATA | 4/10 (0.4) | 0/10 (0.0) | NO DATA |
| | B4 | 4/10 (0.4) | 17/10 (1.7) | 35/10 (3.5) | NO DATA |

This experiment demonstrates the utility of B4 media with different cultivars and when used with different initiation media.

9.5. Rooting

The normalized shoots which were produced above are rooted and grown as in Example 8.

Example 10

10.1. Explant Source

Mature seeds of Capsicum annuum cv.s VegiSweet 89300-1 (DNA Plant Technology Corp., Cinnaminson, N.J.) were surface sterilized in a solution containing 20% household bleach for about 30 minutes on a rotary shaker (50 rpm). The seeds were then rinsed three times in sterile deionized water and placed in 4 oz. culture jars containing 25 mg/l of hormone free MS medium. The seeds were planted at 5 seeds per jar. These germination cultures were placed under constant illumination (40Em-2s 40 $\mu$gEM$^{-2}$ S$^{-1}$—1) at 25° C. Seeds germinated within 10–15 days.

10.2. Preparation of Explants/Shoot Induction

Cotyledons were excised from young seedlings about 3 days following their emergence from the seedcoats. Cotyledons were sliced along the cotyledon edges to form a rectangular explant which was placed (abaxial side down) in dishes containing a medium the same as 10BI except BA was 4 mg/l and IAA was 8 mg/l (IAA was added prior to autoclaving). These shoot induction cultures were placed under the same conditions as the germinating seed. Shoot buds were observed along the margins of the explants after about three weeks of culture.

10.3. Shoot Elongation

After about 3 weeks on shoot induction medium (10BI) explants were transferred to a medium that was the same as B4 except GA$_3$ was 15 mg/l and silver thiosulfate was 30 $\mu$M. Explants were transferred to fresh shoot elongation medium every 2 weeks and cultures were incubated under the same conditions as seed germination cultures except light intensity was decreased to 20 $\mu$Em$^{-2}$S$^{-1}$.

10.4. Shoot maturation/Plantlet Development

After two transfers (about 4 weeks) the shoots were excised from the explant tissue and placed on MSOT media. The shoots resembled axillary shoots of mature soil-grown plants (slightly elongated stem axis with several small unexpanded leaves). Cultures were incubated under the same conditions as shoot elongation cultures. After about two weeks on MSOT medium shoots became morphologically normal.

10.5. Results

Fifteen (15) plantlets were transferred to OMSSN medium for rooting under conditions identical to those used for seed germination cultures; roots formed after about 4 weeks. These plantlets were transferred to soil and acclimated for growth in the greenhouse. Under greenhouse conditions these plantlets developed normally into plants forming additional leaves and eventually flowers. Flowers were normal in appearance and function as evidenced by the production of viable seed. From 15 explants, the mean number of mature shoots per explant was 2.0 (a total of 30 whole plants were regenerated).

Example 11

This example was performed as in Example 10, except that the pepper variety Bell-Sweet was used and the following modifications were made to the 10BI medium at induction stage: 4 mg/l KIN replaced 10 mg/l BA and 1 mg/l NAA replaced 1 mg/l IAA. In this example, from a total of 15 explants, the mean number of mature shoots per explant was 1.6 (total of 24 whole plants were produced).

Example 12

This example was performed as in Example 10, except that the variety used was Italian Gold, and the following modifications were made to the 10BI medium at induction stage: 4 mg/l 2-ip replaced 10 mg/l BA and 1 mg/l IBA replaced 1 mg/l IAA. In this example, from a total of 15 explants, the mean number of mature shoots per explant was 2.2 (a total of 33 whole plants were produced).

Example 13

This example was performed as in Example 10, except that the variety was Italian Gold, and the following modifications were made to the 10BI medium at induction stage: 4 mg/l BA was used and 0.5 mg/l 2,4-D replaced 1 mg/l IAA. In this example, from a total of 15 explants, the mean number of mature shoots per explant was 0.7 (a total of 10 whole plants were produced).

Example 14

This example was performed as in Example 10, except that the variety used was Corona, and true leaves replaced expanded cotyledons as the explant tissue. Leaves were excised from the seedlings about 15 days after cotyledons were removed. Leaves were prepared in a manner identical to cotyledons except that leaf mid ribs were excised from the explant tissue. Also, the following modifications were made to 10BI medium at induction stage: 4 mg/l BA and 8 mg/l IAA were used. In this example, from a total of 15 explants, the mean number of mature shoots per explant was 3.1 (a total of 46 whole plants were produced).

Example 15

This example was performed as in Example 10, except that 5 mg/l GA was used in the B4 medium at elongation stage. In this example, from a total of 15 explants, the mean number of mature shoots per explant was 3.0 (a total of 45 whole plants were produced).

Example 16

This example was performed as in Example 10, except that the cultivar was Super Red Pimento (Stokes Seed Co., Buffalo, N.Y.). In this example, from a total of 15 explants, the mean number of mature shoots per explant was 1.9. A total of 28 plants were regenerated and each was transferred to soil and grown in the greenhouse. Plants were screened for ploidy according to the method of I. Ho et al. supra. A total of four had a stomatal chloroplast number of at least 28. The progeny of these four plants were analyzed for chromosome number according to R. A. Morrison et al. supra. The progeny of three of the four plants had 48 chromosomes (tetraploid); the progeny of the fourth plant had 24 chromosomes (diploid) identical to a diploid control plant of Super Red Pimento.

Although the foregoing invention has been described in detail for purposes of clarity of understanding, it will be obvious that certain modifications may be practiced within the scope of the appended claims.

What is claimed is:

1. A method for genetically transforming a pepper plant, said method comprising:
   (a) cocultivating explant material from the pepper plant with *Agrobacterium tumefaciens* or *rhizogenes* cells carrying an exogenous DNA sequence wherein the explant material is selected from the group consisting of young embryonic cotyledons and young expanded cotyledons;
   (b) selecting and inducing shoots from the explant material from step (a), wherein said shoots are obtained from non-callus material and express the exogenous DNA sequence; and
   (c) elongating and further selecting the shoots from step (b).

2. A method as in claim 1, wherein the shoots are selected and induced in a medium containing an amount of BA chosen to induce shoot regeneration.

3. A method as in claim 2, wherein the amount of BA is about 5 to 20 mg/l when the explant material is young expanded cotyledons and about 0.5 to 5 mg/l when the explant material is young embryonic cotyledons.

4. A method as in claim 1, wherein the shoots are selected and induced in a medium containing an amount of a sulfonylurea herbicide.

5. A method as in claim 1, wherein the shoots are elongated and selected in a medium containing a gibberellin in the amount of about 0.1 to 50 mg/l.

6. A method as in claim 5, wherein the gibberellin is $GA_3$.

7. A method as in claim 1, wherein the shoots are elongated and selected in a medium containing an inhibitor of ethylene action.

8. A method as in claim 7, wherein the inhibitor of ethylene action is $Ag+$.

9. A method as in claim 1, wherein the exogenous DNA includes a plant selectable marker gene selected from the group consisting of aadA, NPTII, NPT, SPT, and ALS.

10. A method as in claim 1, further comprising (d) rooting the shoots from step (c).

11. A method for genetically transforming a pepper plant, said method comprising:
   (a) obtaining the explant material from the pepper plant seed;
   (b) cocultivating the explant material obtained in step (a) with *Agrobacterium tumefaciens* or *rhizogenes* cells carrying an exogenous DNA sequence in a cocultivation medium for a time and under conditions selected to effect transfer of the exogenous DNA sequence to cells of the explant material obtained in step (a), wherein the explant material is selected from the group consisting of young embryonic cotyledons and young expanded cotyledons;
   (c) removing the Agrobacterium cells from the explant material obtained in step (a);

(d) selecting and inducing shoots from the explant material from step (c) in a selection/induction medium for a time and under conditions chosen to produce shoots from non-callus regions of the explant material and select shoots which express the exogenous DNA sequence, wherein the elongation/selection medium contains a gibberellin in the amount of about 0.1 to 50 mg/l and an inhibitor of ethylene action;

(e) elongating and further selecting the shoots from step (d) in an elongation/selection medium; and (f) rooting the selecting regenerated shoots from step (e) in a rooting medium.

12. A method as in claim 11, wherein the cocultivation medium contains nutrients, an energy source, and a virulence induction compound.

13. A method as in claim 12, wherein the cocultivation medium further contains a cytokinin.

14. A method as in claim 11, wherein removing comprises washing the explant material with an anti-Agrobacterium antibiotic.

15. A method as in claim 11, wherein the exogenous DNA sequence includes a plant selectable marker and the selection/induction medium further contains a plant selection agent which inhibits growth of plant material not expressing said marker.

16. A method as in claim 15, wherein the plant selectable marker is selected from the group consisting of aadA, NPTII, HPT, SPT, and ALS and the plant selection agent is selected from the group consisting of spectinomycin, kanamycin, hygromycin, streptomycin, and chlorsulfuron, respectively.

17. A method as in claim 15, wherein the selection/induction medium contains a sulfonylurea herbicide.

18. A method as in claim 11, wherein the selection/induction medium contains nutrients, an energy source, and an anti-Agrobacterium antibiotic.

19. A method as in claim 18, wherein the selection/induction medium further contains a cytokinin.

20. A method as in claim 19, wherein the cytokinin is BA in an amount selected to induce shoot regeneration.

21. A method as in claim 20, wherein the amount of BA is about 5 to 20 mg/l when the explant material is young expanded cotyledons and about 0.5 to 5 mg/l when the explant material is young embryonic cotyledons.

22. A method as in claim 11, wherein the gibberellin is $GA_3$.

23. A method as in claim 11, wherein the inhibitor of ethylene action is $Ag^+$.

24. A method as in claim 11, wherein the rooting medium contains nutrients, an energy source, and an auxin.

25. A method for generating a pepper plant, said method comprising:

(a) obtaining young explant material from the pepper plant, wherein the young explant material is selected from the group consisting of embryonic cotyledons and young expanded cotyledons;

(b) inducing shoots from the explant material from step (a) in an induction medium containing BA for a time and under conditions chosen to induce about regeneration from non-callus regions of the explant material; and (c) elongating the shoots from step (b) in an elongation medium containing a gibberellin and an inhibitor of ethylene action.

26. A method as in claim 25, wherein the amount of BA is about 5 to 20 mg/l when the explant material is young expanded cotyledons and about 0.5 to 5 mg/l when the explant material is young embryonic cotyledons.

27. A method as in claim 25, wherein the shoots are elongated in a medium containing a gibberelin in the amount of about 0.1 to 25 mg/l.

28. A method as in claim 27, wherein the gibberelinn is $GA_3$.

29. A method as in claim 25, wherein the inhibitor of ethylene action is $Ag^+$.

30. A method as in claim 25, further comprising (d) rooting the shoots from step (c).

31. A method for regenerating a pepper plant, said method comprising:

(a) obtaining young explant material from a pepper plant seed;

(b) inducing shoots from the young explant material from step (a) in an induction medium containing BA for a time and under conditions chosen to induce shoot regeneration from non-callus regions of the explant material, wherein the young explant material is selected from the group consisting of embryonic cotyledons and young expanded cotyledons;

(c) elongating the shoots from step (b) in an elongation medium containing a gibberellin and an inhibitor of ethylene action; and (d) rooting the shoots from step (c) in a rooting medium.

32. A method as in claim 31, wherein the induction medium contains nutrients and an energy source.

33. A method as in claim 31, wherein the amount of BA is about 5 to 20 mg/l when the explant material is young expanded cotyledons and about 0.5 to 5 mg/l when the explant material is young embryonic cotyledons.

34. A method as in claim 31, wherein the gibberelin is present in the elongation medium at a concentration from about 0.1 to 25 mg/l.

35. A method as in claim 34, wherein the gibberelin is $GA_3$.

36. A method as in claim 31, wherein the inhibitor of ethylene action is $Ag^+$.

37. A method as in claim 31, wherein the rooting medium contains nutrients, an energy source, and an auxin.

* * * * *